United States Patent
O'Neil et al.

(10) Patent No.: US 6,709,461 B2
(45) Date of Patent: Mar. 23, 2004

(54) MODULAR JOINT PROSTHESIS SYSTEM

(75) Inventors: Michael J. O'Neil, Mansfield, MA (US); Joseph Kennedy, Lakeville, MA (US); James Boyko, Attleboro, MA (US); George Cipolletti, Duxbury, MA (US)

(73) Assignee: DePuy Products, Inc., Warsaw, IN (US)

( * ) Notice: Subject to any disclaimer, the term of this patent is extended or adjusted under 35 U.S.C. 154(b) by 0 days.

(21) Appl. No.: 10/071,715

(22) Filed: Feb. 7, 2002

(65) Prior Publication Data

US 2002/0072802 A1 Jun. 13, 2002

Related U.S. Application Data

(62) Division of application No. 09/243,260, filed on Feb. 3, 1999, now abandoned.

(51) Int. Cl.[7] .................................................. A61F 2/38
(52) U.S. Cl. .................................................. 623/20.33
(58) Field of Search ........................... 623/20.33, 20.29, 623/20.28, 20.27, 20.31, 20.14, 20.15, 20.16–20.26, 20.3, 20.32, 21.11–21.19

(56) References Cited

U.S. PATENT DOCUMENTS

| | | | |
|---|---|---|---|
| D248,771 S | * 8/1978 | Groth, Jr. et al. | D24/33 |
| 4,219,893 A | 9/1980 | Noiles | 3/1.911 |
| 4,257,129 A | * 3/1981 | Volz | 3/1.911 |
| 4,301,553 A | 11/1981 | Noiles | 3/1.911 |
| 4,673,407 A | * 6/1987 | Martin | 623/20 |
| 4,769,039 A | 9/1988 | Horber | 623/20 |
| 5,019,103 A | 5/1991 | Van Zile et al. | 623/20 |
| 5,059,216 A | 10/1991 | Winters | 623/20 |
| 5,062,852 A | 11/1991 | Dorr et al. | 623/20 |
| 5,071,438 A | 12/1991 | Jones et al. | 623/20 |
| 5,171,283 A | 12/1992 | Pappas et al. | 623/20 |
| 5,194,066 A | * 3/1993 | Van Zile | 623/20 |
| 5,395,401 A | 3/1995 | Bahler | 623/20 |

(List continued on next page.)

FOREIGN PATENT DOCUMENTS

| | | | |
|---|---|---|---|
| EP | 0495340 | 7/1992 | A61F/2/38 |
| EP | 512529 | 11/1992 | |
| EP | 0529408 | 3/1993 | A61F/2/38 |
| EP | 0531263 | 3/1993 | A61F/2/38 |
| EP | 0627202 | 12/1994 | A61F/2/38 |
| EP | 0631764 | 1/1995 | A61F/2/30 |
| EP | 724868 | 8/1996 | |
| EP | 0781534 | 7/1997 | A61F/2/38 |
| FR | 2716619 | 9/1995 | A61F/2/38 |
| WO | WO 9420047 | 9/1994 | A61F/2/38 |
| WO | WO 9709939 | 3/1997 | A61B/17/58 |

*Primary Examiner*—Corrine McDermott
*Assistant Examiner*—Alvin Stewart
(74) *Attorney, Agent, or Firm*—Nutter McClennen & Fish LLP

(57) ABSTRACT

A modular joint prosthesis includes a tibial component that may be rotatable or non-rotatable. The system includes a tibial bearing insert having surface features, either male or female, that are able to be slidably mated to complementary surface features of another component. In one embodiment, the tibial component is non-rotatable and the surface features of the tibial bearing insert are slidably matable to complementary surface features of a tibial plateau. In another embodiment the tibial component is rotatable and the surface features of the tibial bearing insert are slidably matable to complementary surface features of a rotating platform base. The rotating platform base, in turn, is rotably mounted to a tibial plateau. The system may utilize a securing member to prevent translation motion between the tibial bearing insert and the tibial plateau or the tibial bearing insert and the rotatable platform base.

27 Claims, 5 Drawing Sheets

U.S. PATENT DOCUMENTS

| | | | |
|---|---|---|---|
| 5,413,605 A | 5/1995 | Ashby et al. | 623/20 |
| 5,489,311 A | 2/1996 | Cipolletti | 623/20 |
| 5,609,641 A | 3/1997 | Johnson et al. | 623/20 |
| 5,645,604 A * | 7/1997 | Schneider et al. | 623/20 |
| 5,683,469 A | 11/1997 | Johnson et al. | 623/20 |
| 5,776,200 A | 7/1998 | Johnson et al. | 623/20 |
| 5,824,101 A * | 10/1998 | Pappas | 623/20.33 |
| 5,824,103 A * | 10/1998 | Williams | 623/20.32 |
| 5,957,979 A * | 9/1999 | Beckman et al. | 623/20 |
| 6,139,581 A * | 10/2000 | Engh et al. | 623/20.34 |

\* cited by examiner

MODULAR JOINT PROSTHESIS SYSTEM

CROSS-REFERENCE TO RELATED APPLICATIONS

Not Applicable.

STATEMENT REGARDING FEDERALLY SPONSORED RESEARCH

Not Applicable.

BACKGROUND OF THE INVENTION

The invention relates to joint prostheses. More particularly, the invention is directed to tibial components of knee joint prostheses that can be configured to be either rotatable or non-rotatable.

Joint replacement surgery is quite common and it enables many individuals to function normally when otherwise it would not be possible to do so. Artificial joints usually comprise metallic, ceramic and/or plastic components that are fixed to existing bone.

Knee arthroplasty is a well known surgical procedure by which a diseased and/or damaged natural knee joint is replaced with a prosthetic knee joint. Typical knee prostheses include a femoral component, a patella component, a tibial tray or plateau, and a tibial bearing insert. The femoral component generally includes a pair of laterally spaced apart condylar portions, the distal surfaces of which articulate with complementary condylar elements formed in a tibial bearing insert.

The tibial plateau is mounted within the tibia of a patient. Typically, the tibial bearing insert, which is usually made of ultra high molecular weight polyethylene (UHMWPE), is mounted upon the superior surface of the tibial plateau. The geometry and structure of the tibial bearing insert varies depending upon the needs and joint condition of a patient. Some tibial bearing inserts are designed to be used with joint prostheses that are implanted during procedures that retain the cruciate ligaments. Others are implanted after removal of the cruciate ligaments, and are thus structured to compensate for the loss of these ligaments. Yet other tibial bearing inserts are used with prostheses that provide enhanced stabilization to the knee joint. In addition to the geometry that may be assumed by a tibial bearing insert of a joint prosthesis, the tibial bearing insert may be designed so as to be fixed or rotatable with respect to the tibial plateau upon which it is mounted.

Rotatable knee prosthesis may be indicated in cases where a surgeon believes that forces placed on the prosthesis during normal daily use may lead to abnormal contact or the displacement or dislocation of the insert from the tibial tray. To accommodate these forces, and to reduce the chances for dislocation, some tibial components of knee prostheses have been designed to allow rotation of the tibial bearing insert relative to the proximal or superior surface of the tibial tray about the longitudinal axis of the prosthesis. Such rotation can increase the contact area between the femoral condyles and the tibial bearing insert throughout the range of knee motion, thus reducing stress on the tibial bearing insert.

Various designs for rotatable tibial components of knee joint prostheses are known in the art. For example, U.S. Pat. No. 4,219,893 (Noiles) and U.S. Pat. No. 4,301,553 (Noiles) disclose knee joint prostheses in which the tibial component comprises a tibial plateau having a bearing surface with a recessed region within which the tibial bearing insert may rest. Sufficient clearance is provided in the bearing surface of the tibial plateau to allow some medial-lateral rotation of the tibial bearing insert with respect to the tibial plateau. Other patents that disclose tibial components of knee joint prostheses in which a tibial bearing insert is rotatable with respect to the tibial plateau are disclosed in U.S. Pat. No. 5,059,216 (Winters); U.S. Pat. No. 5,071,438 (Jones et al); U.S. Pat. No. 5,171,283 (Pappas et al); and U.S. Pat. No. 5,489,311 (Cipolletti).

It is not normally possible for a surgeon to make a final determination in advance of surgery the type of knee prosthesis system that will best suit a patient. This decision usually is not made until the condition of the knee is assessed in the course of surgery.

As a result of the numerous candidate designs for knee joint prostheses, several prosthesis components of differing designs may be used or trialed during a surgical procedure before the appropriate components are selected. Accordingly, a large inventory of parts is required during a joint replacement surgical procedure, thus adding to the cost of surgery.

Despite the existing designs for knee joint prostheses having a rotatable tibial component, there remains a need for prostheses that allow rotation of the tibial bearing insert to accommodate the stresses placed upon the knee. At the same time, such tibial bearing inserts should possess sufficient axial securement so as to decrease or eliminate the possibility of subluxation of the tibial bearing insert.

It would thus be advantageous to provide a joint prosthesis system that utilizes modular prostheses components that are able to be configured to form either rotatable or non-rotatable prostheses from the same collection of modular parts. Such a system would effectively reduce the overall inventory count and reduce the inventory carrying costs associated with joint replacement surgery.

SUMMARY OF THE INVENTION

The present invention provides a rotatable knee joint prosthesis system which utilizes modular components to enable the prosthesis system to be made rotatable or non-rotatable.

The prosthesis system of the invention comprises at least one tibial bearing insert which has a top, articulating surface with at lease one concavity formed therein, and a bottom, mating surface. The bottom, mating surface includes at least one elongate dovetail element, which can be either a male or female dovetail element. Preferably, a bore is substantially centrally disposed in the tibial bearing insert, and it extends from the top to the bottom surfaces thereof.

The system also includes a tibial plateau which has a bottom, bone engaging surface and a top surface having a substantially centrally located tibial plateau bore. The top surface of the tibial plateau also includes at lease one complementary dovetail element that is slidably matable with the elongate dovetail element of the tibial bearing insert. Mating of the dovetail elements of the tibial bearing insert and the tibial plateau joins these components together in such a way that the tibial bearing insert is non-rotatably mounted to the tibial plateau. The system may also include an elongate securing member that is mountable within both the tibial plateau bore and the tibial bearing insert bore to prevent any linear movement (i.e., translation) of the tibial bearing insert in the medial-lateral and anterior-posterior directions independent of the tibial plateau. The elongate element can be in the form of a bolt member or a relatively small diameter dowel.

In another embodiment, the components of the prosthesis system can be configured to form a modular, rotatable tibial prosthesis component. This embodiment utilizes an essentially identical tibial bearing insert structure, which is joined to a rotating platform base and a tibial plateau. The rotating platform base has a bottom, articulating surface that includes a mating stem member extending distally therefrom, and a top surface that has a substantially centrally located rotating platform base bore. Further, the top surface of the rotating platform base includes at least one elongate complementary dovetail element that is slidably matable with the dovetail element of the tibial bearing insert such that the tibial bearing insert is non-rotatably mounted to the rotating platform base. This system also includes an elongate securing member that is mountable within both the rotating platform base bore and the tibial bearing insert bore to prevent any linear movement (i.e., translation) of the tibial bearing insert in the medial-lateral and anterior-posterior directions independent of the rotating platform base.

The tibial plateau includes a top surface with a mounting cavity formed therein and a bottom surface having a bone engaging mounting stem extending distally therefrom. The mounting cavity has dimensions that are sufficient to accept the mating stem member of the rotating platform base such that the rotating platform base is able to rotate in either a clockwise or counterclockwise direction relative to the tibial plateau.

The modular prosthesis system of the invention may include a variety of components that are present in different sizes and geometries. That is, the system may be provided with different sized tibial bearing inserts, and tibial bearing inserts having structures and functionalities that render them useful for different patient conditions. Kits provided to surgeons may include a sufficient number of components to allow assembly of a rotatable or non-rotatable tibial component prosthesis.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
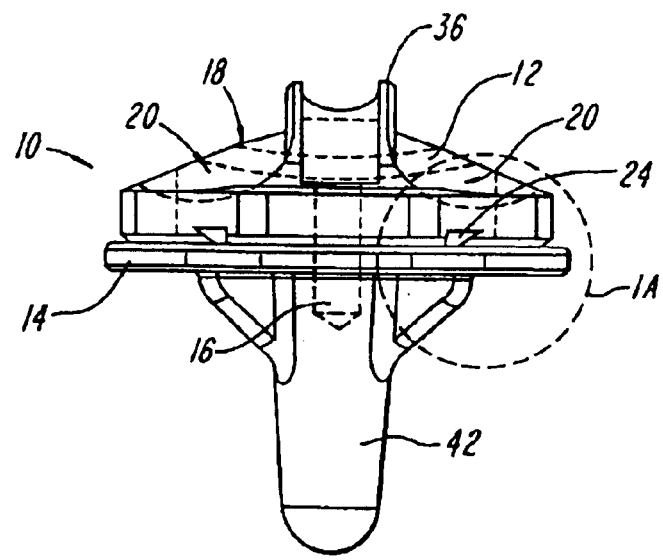
FIG. 1 is posterior view of a representative non-rotatable tibial prosthesis according to the present invention.
Figure 1A:
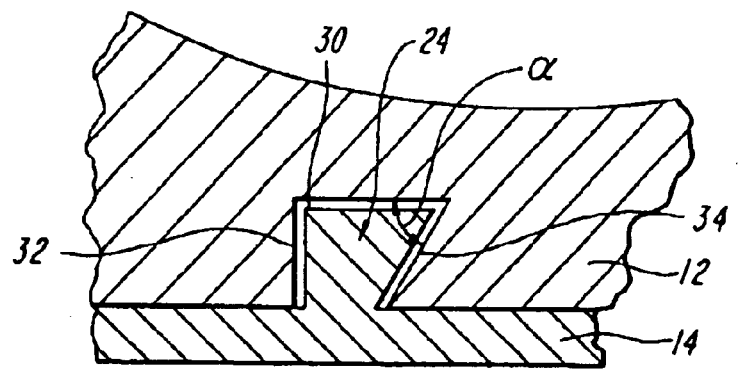
FIG. 1A is a detail sectional view of a portion of FIG. 1.

The invention provides a modular tibial component for a joint prosthesis system. The modularity of the system allows basic components to be used in various combinations to yield both rotatable and non-rotatable components. That is, the same design for a tibial bearing insert can be used with various modular components to form both rotatable and non-rotatable prostheses. This feature helps to reduce overall part inventory and to reduce the costs of replacement surgery.

FIGS. 1–3A illustrate a non-rotatable tibial component 10 of a joint prosthesis system which includes a tibial bearing insert 12, a tibial plateau 14 and a securing member 16.

The tibial bearing insert 12 has a top surface 18, that includes at least one concavity 20 and which articulates with a femoral component (not shown). The bottom surface 22 of the tibial bearing insert 12 includes at least one dovetail element 24. Further, a bore 26 extends through the tibial bearing insert from the top to the bottom surfaces 18, 22 of the tibial bearing insert. The diameter of the bore may be in the range of about 2 to 8 mm. The dovetail element 24 may be a male or female dovetail element and it may extend either in the anterior-posterior or medial-lateral directions. In the illustrated embodiment two parallel, female dovetail elements are provided, each extending in the anterior-posterior direction.

The female dovetail element 24, illustrated in FIGS. 1–3A, may be of a substantially trapezoidal cross-section having an open face 28 on the bottom surface 22 of tibial bearing insert 12, a base wall 30 that is substantially parallel to bottom surface 18, a sidewall 32, and a canted sidewall 34. Preferably, the dovetail element 24 extends over substantially the entire bottom surface 22 of the tibial bearing insert, from anterior edge 33 to posterior edge 35. The dimensions of dovetail element 24 may vary depending on the requirements of a given application. However, in an exemplary embodiment the open face 28 may span a distance of about 2 to 6 mm while the depth of the dovetail element (measured from bottom surface 22 to base wall 30) is about 2 to 6 mm. The canted sidewall 34 may be oriented at an angle ($\alpha$) of about 15° to 45°.

The system of the invention may include a variety of known types of tibial bearing inserts, each suited for a different knee prosthesis functionality. Although FIGS. 1–9 illustrate a tibial bearing insert having an elevated spine member 36, other types of tibial bearing inserts, such as those without spines or those with different sized or shaped spines, may be used as well. For example, the tibial bearing insert may be a cruciate retaining insert, a cruciate sacrificing insert, or a stabilizing insert. In the case of cruciate sacrificing and stabilizing inserts that include raised spine members, the height of the spine member may be in the range of about 5 to 30 mm.

The tibial plateau 14 used with rotatable tibial component 10 includes a top surface 38 and a bottom surface 40. The bottom surface preferably includes a distally extending mounting stem 42 that is mountable within a prepared cavity formed in a patient's tibia in a manner known in the art. A bore 44 is formed in the tibial plateau, extending from top surface 38 into the mounting stem 42. The bore typically has depth of about 5 to 25 mm and a diameter of about 2 to 8 mm.

The top surface 38 of tibial plateau 14 includes at least one complementary dovetail element 44 which is slidably matable with the dovetail element 24 formed in the tibial bearing insert 12. As noted above, the dovetail element 14 of the tibial bearing insert may be either male or female. By use of the term "complementary" with respect to the complementary dovetail element 44 formed in the tibial plateau, it is understood that the type of dovetail formed on the tibial plateau 14 is the opposite of that formed in the tibial bearing insert 12. That is, if a female dovetail element is formed in a tibial bearing insert, a male dovetail is formed on the tibial plateau.

In the illustrated embodiment, the complementary dovetail 44 is a male dovetail. As such, it is raised above the top surface 38 of the tibial plateau 14. One or more complementary dovetails 44 may be present on the top surface 38 of the tibial plateau 14. Preferably, the number of complementary dovetails 44 corresponds to the number of dovetails 24. Further, the complementary dovetail 44 preferably extend parallel to one another and extend in the anterior-posterior direction or the medial-lateral direction. One of ordinary skill in the art will readily understand that the complementary dovetail elements 44 should be positioned on the tibial plateau 14 so as to be aligned with the dovetail elements 24 present in the tibial bearing insert 12. In the illustrated embodiment, two parallel, male complementary dovetail elements 44 are used, each extending over the entire top surface 38 of the tibial plateau 14 from anterior edge 46 to posterior edge 48.

The complementary dovetail element 44 is preferably raised to a height (H) of about 2 to 6 mm above top surface 38. The complementary dovetail element includes a top wall 50, a sidewall 52, and a canted sidewall 54. One of ordinary skill in the art will appreciate that the dimensions of complementary dovetail elements 44 must be such that they are able to matingly slide within the dovetail elements 24 of tibial bearing insert 12. In an exemplary embodiment, the width of the top wall 50 preferably is in the range of about 3 to 8 mm while the canted sidewall 54 extends at an angle of about 15° to 45°.

The mounting stem 42 formed on the tibial plateau 14 is of a type that is well known in the art and its shape and dimensions can be readily ascertained by one of ordinary skill in the art.

Figure 2:
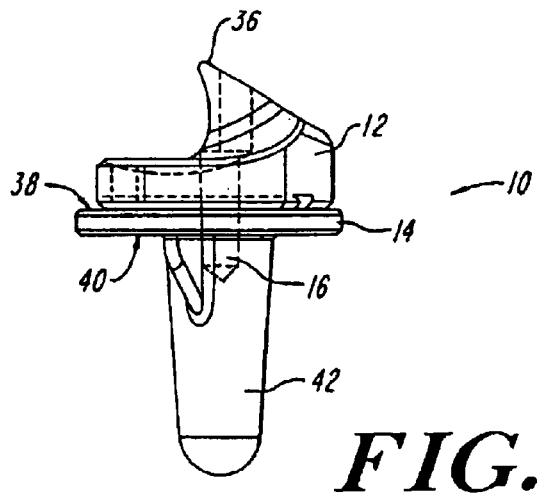
FIG. 2 is a side elevation view of the prosthesis of FIG. 1.
Figure 3A:
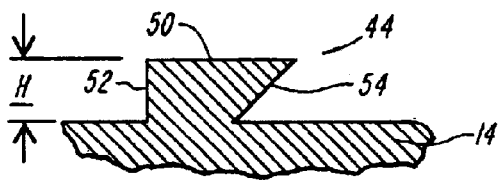
FIG. 3A is a detail section view of a portion of FIG. 3.
Figure 3:
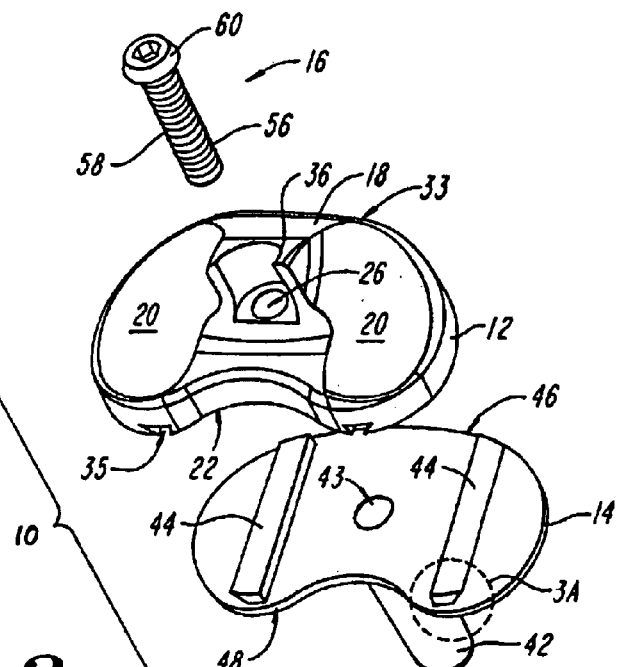
FIG. 3 is a perspective, unassembled view of the prosthesis of FIG. 1.

The tibial component may further include a securing member 16 that is able to join the tibial bearing insert 12 and the tibial plateau 14 in such a way as to prevent any translational movements of these components with respect to each other. As shown in FIGS. 1 and 2, once the tibial bearing insert and the tibial plateau are joined together the securing member is inserted through the bore 26 in the tibial bearing insert 12 and into the cavity 43 of the tibial plateau 14. As so positioned, the securing member 16 essentially locks the tibial bearing insert 12 and the tibial plateau 14 together, preventing any relative translational movement of these two elements.

The securing member 16 can take a variety of shapes and forms. Obviously, the securing member 16 should have dimensions that enable it to be mounted within bore 26 and cavity 43 in a frictional fit. In one embodiment, illustrated in FIGS. 1–3, the securing member 16 can be in the form of a bolt member 56. The bolt member 56 includes an elongate shaft 58 that extends from a head portion 60. The head portion 60 should have dimensions that enable it to fit within a seating area 62 formed on the top surface 18 of the tibial bearing insert 12. In an exemplary embodiment, the bolt member has an overall length of about 5 to 45 mm with an elongate shaft length of about 5 to 30 mm and a head length of about 3 to 5 mm. The diameter of the bolt member is preferably in the range of about 2 to 6 mm.

Figure 7:
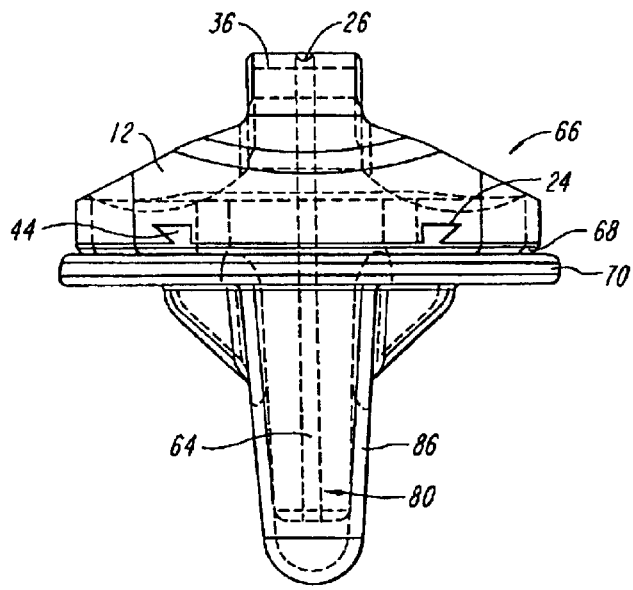
FIG. 7 is an anterior view of an alternative rotatable tibial component according to the present invention.
Figure 8:
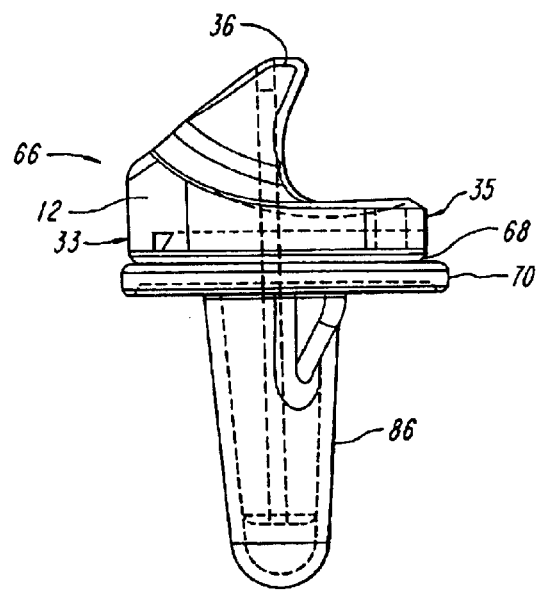
FIG. 8 is a side elevation view of the prosthesis of FIG. 7.
Figure 9:
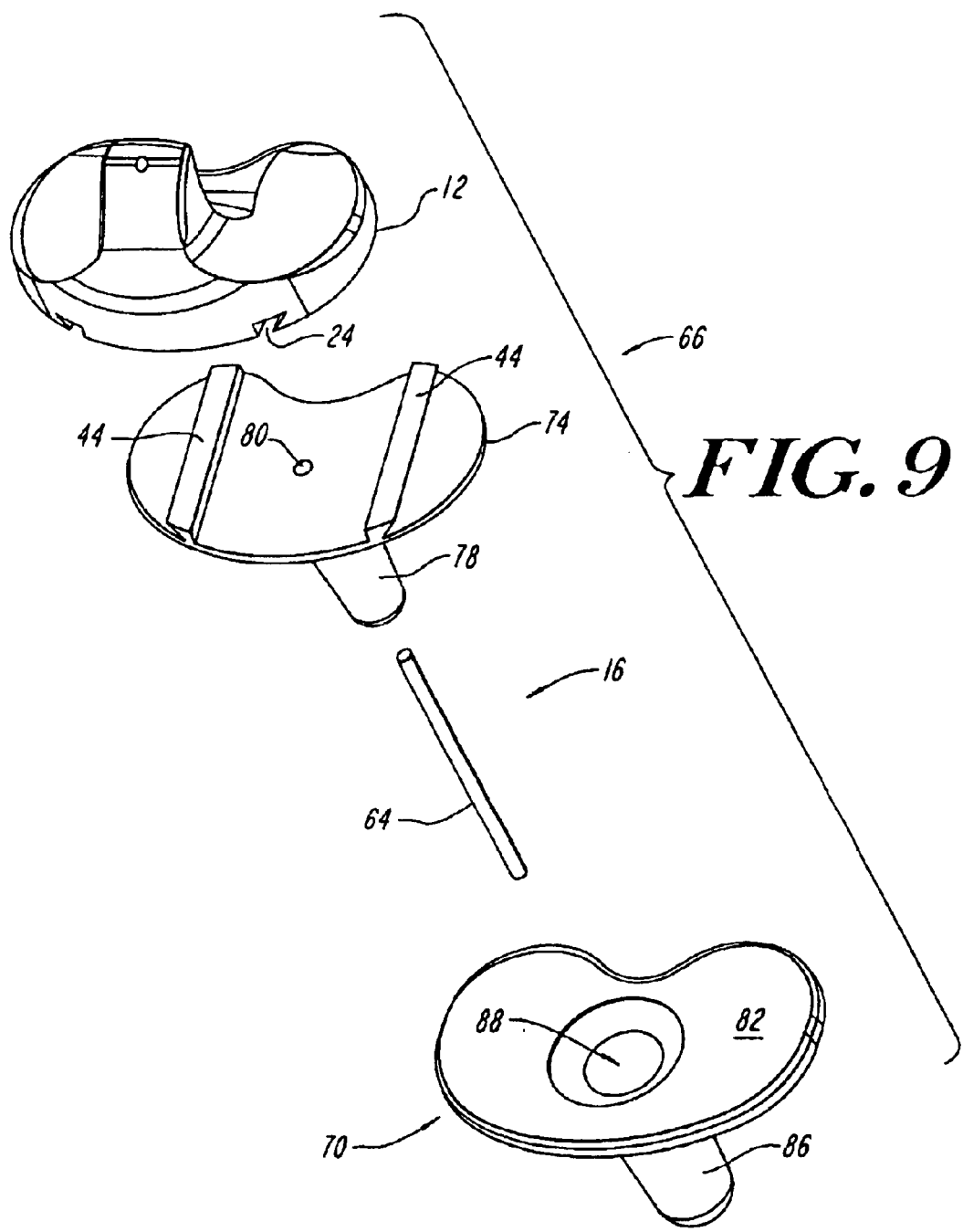
FIG. 9 is a perspective, unassembled view of the prosthesis of FIG. 7.

In another embodiment, illustrated in FIGS. 7–9, the securing member 16 may be in the form of a dowel 64 that likewise may be positioned within bore 26 and cavity 43.

Although FIGS. 7–9 illustrate the use of a dowel 64 as a securing member 16 with a rotatable tibial component, one of ordinary skill in the art will understand that the use of a dowel is equally applicable to non-rotatable tibial components as well.

Figure 4:
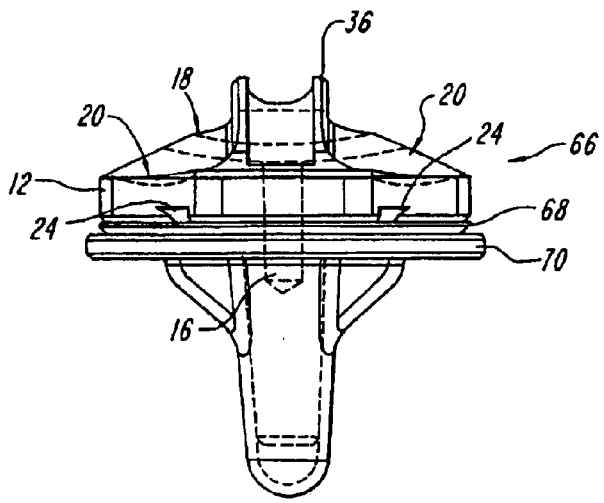
FIG. 4 is a posterior elevation view of and alternative, rotatable tibial prosthesis component according to the present invention.
Figure 5:
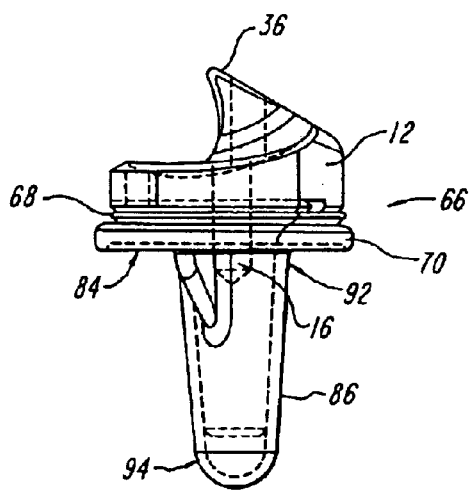
FIG. 5 is a side elevation view of the prosthesis of FIG. 4.
Figure 6:
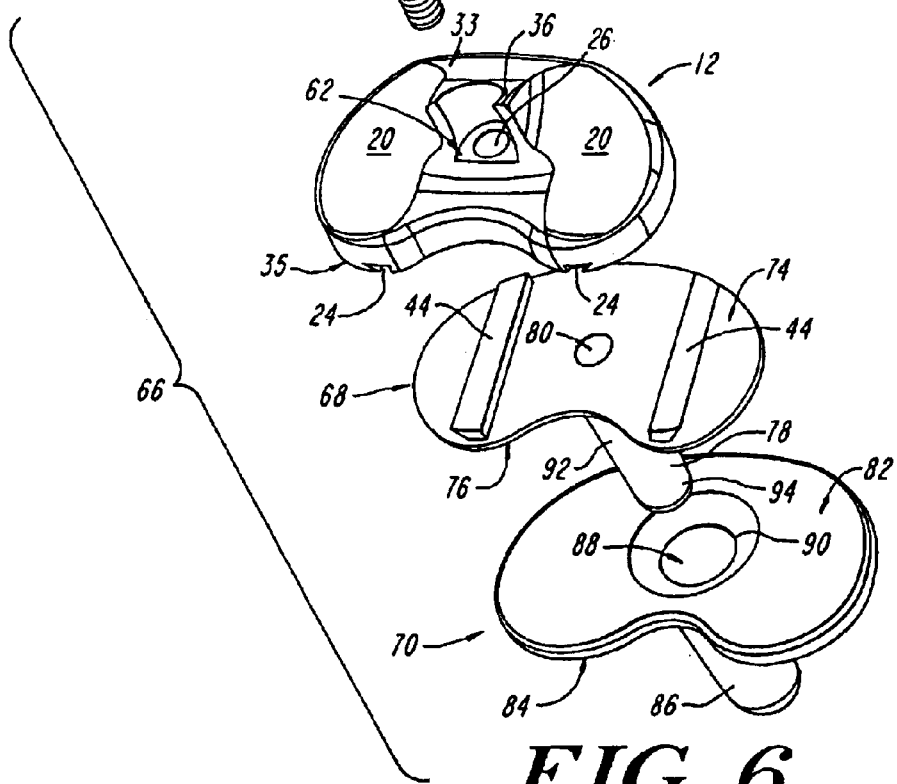
FIG. 6 is a perspective, unassembled view of the prosthesis of FIG. 4.

FIGS. 4–6 illustrate a rotatable tibial component 66 which includes a tibial bearing insert 12 of a type that is virtually identical to that described above with respect to FIGS. 1–3A, a rotating platform base 68, a tibial plateau 70, and a securing member 16.

As noted above, the tibial bearing insert 12 is virtually identical to that described above with respect to FIGS. 1–3A.

The rotating platform base 68 includes a top surface 74 and a bottom surface 76. A mating stem 78 extends distally from the bottom surface 76 of the rotating platform base 68. Further, a bore 80 is substantially centrally located within the rotating platform base. Bore 80 extends through the rotating platform base 68 from top surface 74 and into the mating stem 78. The bore 80 may be a blind bore as shown in FIGS. 4–6, or it may extend entirely through the mating stem 78 of the rotating platform base as shown in FIGS. 7–9.

The top surface 74 of the rotating platform base 68 further includes complementary dovetail elements 44 which are identical to those described above with respect to FIGS. 1–3A. While FIGS. 1–3A illustrate the complementary dovetail elements 44 mounted on the top surface of tibial plateau 14, FIGS. 4–9 illustrate the complementary dovetail element 44 mounted on a top surface 74 of rotating platform base 68.

The tibial plateau 70 used with the rotatable tibial component 66 includes a top surface 82 and a bottom surface 84. A mounting stem 86, similar in structure and dimensions to mounting stem 42, preferably extends distally from the bottom surface 84. A mating cavity 88, formed in the top surface of the tibial plateau 70, extends from an opening 90 on the top surface 82 of tibial plateau 70 and terminates an end wall (not shown) within the mounting stem 86. One of ordinary skill in the art will readily appreciate that the mating cavity should have dimensions that enable the mating stem 78 of the rotating platform base 68 to be seated therein while allowing the rotating platform base 68 to be capable of rotational movement relative to tibial plateau 70.

The mating stem 78 preferably has a length of about 10 to 40 mm and tapers inwardly from a proximal end 92 to a distal end 94 thereof. The diameter of the mating stem 78 at its widest point is in the range of about 10 to 25 mm, and the diameter tapers to about 5 to 20 mm at its narrowest point.

As noted above, the dimensions of the mating cavity 88 should be sufficient to rotatably seat mating stem 78. Accordingly, the depth of the mating cavity is preferably about 10 to 40 mm, and the mating cavity has a diameter that tapers from a diameter at its widest, proximal portion of about 10 to 25 mm to a diameter of about 5 to 20 mm at its narrowest, distal portion.

The securing member 16 is also used with rotatable tibial component 66 to prevent relative translation between the tibial bearing insert 12 and the rotatable platform base 68. FIGS. 4–6 illustrate an embodiment of the invention in which the securing member 16 is a bolt 56 of the type described above with respect to FIGS. 1–3A. FIGS. 7–9 illustrate another embodiment of the invention, also described above, in which the securing element 16 is an elongate dowel 64. Once the tibial bearing insert 12 and the rotating platform base 68 are mated to one another, dowel 64 may be inserted through bore 26 formed in the tibial bearing insert and through the bore 80 formed in the rotating platform base. The relative dimensions of dowel 64 and bores 26, 80 should be such that a frictional fit is effected. Once the dowel is so positioned, decoupling of the tibial bearing insert and the rotatable platform base is not possible since the interlocking dovetail elements prevent axial separation of these components and the dowel prevents any translational movement which could cause these pieces to separate.

One of ordinary skill in the art will readily understand how to assemble the prosthesis components of the invention. In the case of the non-rotatable tibial component 10 illustrated in FIGS. 1–3A, a suitably sized and shaped tibial bearing insert may be mated to a tibial plateau by aligning these components so that the dovetail elements 24, 44 can be slidably mated. Once the tibial bearing insert is slidably mounted upon the tibial plateau, the securing member 16 (e.g., bolt 56 or dowel 64) is joined between the tibial bearing insert and the tibial plateau 14 to prevent relative translational movement of these components.

Similarly, the rotatable tibial component 66 can be assembled by slidably joining tibial bearing insert 12 to rotatable platform base 68 and subsequently positioning securing member 16 (i.e., bolt 56 or dowel 64) within bores 26, 80 to prevent relatively translational movement between tibial bearing insert 12 and rotating platform base 68. Once these components are assembled, they may be assembled to tibial plateau 70 by seating mating stem 78 within mating cavity 80. Once the tibial bearing insert and the rotatable platform base 12, 68 are seated within the tibial plateau 70, the tibial bearing insert/rotatable platform base assembly is able to rotate with respect to the tibial plateau.

One of ordinary skill in the art will readily appreciate that a variety of materials can be used to manufacture the components of the invention. The tibial plateau is typically made of a metal or metal alloy while the tibial bearing insert is typically made of a polymeric material such as ultra-high molecular weight polyethylene. The rotating platform base may be made of a polymeric material or a metal or metal alloy similar to that used for the tibial plateau. One of ordinary skill in the art will also appreciate that a variety of materials can be used to prepare the securing member. Preferably, the securing member is made from a metal or metal alloy that has a higher modulus than that of the material from which the tibial bearing insert is made.

It is understood that various modifications may be made to the invention described herein without departing from its intended scope. All references cited herein are expressly incorporated by reference in their entirety.

What is claimed is:

1. A joint prosthesis system, comprising:
   at least one tibial bearing insert having a top, articulating surface with at least one concavity formed therein, and a bottom mating surface with
     a substantially centrally located tibial bearing insert bore, and
     at least one dovetail element;
   a rotating platform base having a bottom articulating surface with a stem member extending distally therefrom, and a top surface having
     a substantially centrally located platform base bore, and
     at least one complementary dovetail element matable with the at least one dovetail element of the at least one tibial bearing insert such that the at least one tibial bearing insert is non-rotatably mounted to the rotating platform base;
   an elongate member mountable within both the rotating platform base bore and the tibial bearing insert bore to prevent any translational motion of the at least one tibial bearing insert independent of the rotating platform base; and
   a tibial plateau having a top surface with a mounting cavity formed therein and a bottom surface having a bone-engaging mounting stem extending distally therefrom, the mounting cavity having dimensions sufficient to accept the stem member of the rotating platform base such that the rotating platform base is able to rotate in either a clockwise or counterclockwise direction relative to the tibial plateau.

2. The system of claim 1, wherein the at least one tibial bearing insert comprises a selection of tibial bearing inserts, each having different geometries and functionalities.

3. The system of claim 2, wherein the top surface of the at least one tibial bearing insert includes a spine element protruding therefrom.

4. The system of claim 3, wherein one of the at least one tibial bearing inserts is a cruciate sacrificing insert and the spine element has a height in the range of about 5 to 30 mm.

5. The system of claim 3, wherein one of the at least one tibial bearing inserts is a stabilizing insert and the spine element has a height in the range of about 5 to 30 mm.

6. The system of claim 3, wherein the tibial bearing insert bore extends at least partially into the spine element.

7. The system of claim 3, wherein the rotating platform base bore is a blind bore.

8. The system of claim 7, wherein the platform base bore extends at least partially into the stem member of the rotating platform base.

9. The system of claim 3, wherein the rotating platform base bore extends through the rotating platform base, having a first opening on the top surface thereof and a second opening on a distal end of the mounting stem.

10. The system of claim 1, wherein the tibial bearing insert bore has a diameter in the range of about 2 to 8 mm.

11. The system of claim 10, wherein the elongate member is selected from the group consisting of a dowel and a bolt.

12. The system of claim 1, wherein the at least one elongate dovetail element on the at least one tibial bearing insert is at least one female dovetail.

13. The system of claim 12, wherein the at least one female dovetail extends along the entire bottom surface of the tibial bearing insert in the anterior-posterior direction.

14. The system of claim 13, wherein the at least one female dovetail comprises two parallel female dovetails.

15. The system of claim 13, wherein the at least one female dovetail extends along the entire bottom surface of the tibial bearing insert in the medial-lateral direction.

16. The system of claim 15, wherein the at least one female dovetail comprises two parallel female dovetails.

17. The system of claim 1, wherein the at least one elongate complementary dovetail element is at least one male dovetail.

18. The system of claim 17, wherein the at least one male dovetail extends along the entire top surface of the rotating platform base in the anterior-posterior direction.

19. The system of claim 18, wherein the at least one male dovetail comprises two parallel male dovetails.

20. The system of claim 19, wherein the at least one male dovetail extends along the entire top surface of the rotating platform base in the medial-lateral direction.

21. The system of claim 19, wherein the at least one male dovetail comprises two parallel male dovetails.

22. A joint prosthesis system comprising:

at least one tibial bearing insert having a top, articulating surface with at least one concavity formed therein, and a bottom, mating surface with
- a substantially centrally located tibial bearing insert bore, and
- at least one surface feature extending along the bottom surface in a direction selected from the group consisting of the anterior-posterior direction and the medial-lateral direction;

a rotating platform base having a bottom articulating surface with a stem member extending distally therefrom, and a top surface having
- a substantially centrally located platform base bore, and
- complementary surface feature slidably matable with the at least one surface feature on the at least one tibial bearing insert, wherein the at least one complementary surface feature extends over the top surface in a direction selected from the group consisting of the anterior-posterior direction and the medial-lateral direction;

an elongate member mountable within both the tibial tray bore and the tibial bearing insert bore to prevent any movement of the at least one tibial bearing insert into the medial-lateral and anterior-posterior directions independent of the rotating platform base; and a tibial plateau having a top surface with a mounting cavity formed therein and a bottom surface having a bone-engaging mounting stem extending distally therefrom, the mounting cavity having dimensions sufficient to accept the stem member of the rotating platform base such that the rotating platform base is able to rotate in either a clockwise or counterclockwise direction relative to the tibial plateau.

23. A rotatable joint prosthesis system, comprising:

at least one tibial bearing insert having a top, articulating surface with at least one concavity formed therein, and a bottom mating surface;

a rotating platform base having a top surface rigidly matable to the bottom mating surface of the at least one tibial bearing insert and a bottom, mounting surface having a planar surface and a substantially distally extending mating stem;

a mating element adapted to mate the at least one tibial bearing insert and the rotating platform base to prevent any translational motion of the at least one tibial bearing insert independent of the rotating platform base; and a tibial plateau having a top surface with a mating cavity formed therein and a bottom surface having a bone-engaging mounting stem extending distally therefrom, the mating cavity having dimensions sufficient to accept the mating stem of the rotating platform base such that the rotating platform base is able to rotate in either a clockwise or counterclockwise direction relative to the tibial plateau.

24. The system of claim 23, wherein the at least one tibial bearing insert comprises a selection of tibial bearing inserts, each having different geometries and functionalities.

25. The system of claim 24, wherein the top surface of the at least one tibial bearing insert includes a spine element protruding therefrom.

26. The system of claim 25, wherein one of the at least one tibial bearing inserts is a cruciate sacrificing insert and the spine element has a height in the range of about 5 to 30 mm.

27. The system of claim 25, wherein one of the at least one tibial bearing inserts is a stabilizing insert and the spine element has a height in the range of about 5 to 30 mm.

* * * * *